(12) United States Patent
Yoo et al.

(10) Patent No.: US 8,263,565 B2
(45) Date of Patent: Sep. 11, 2012

(54) NANOEMULSION COMPRISING METABOLITES OF GINSENG SAPONIN AS AN ACTIVE COMPONENT AND A METHOD FOR PREPARING THE SAME, AND A SKIN-CARE COMPOSITION FOR ANTI-AGING CONTAINING THE SAME

(75) Inventors: Byung Hee Yoo, Suwon-shi (KR); Byung Young Kang, Seoul (KR); Myeong Hoon Yeom, Yongin-shi (KR); Dae Seok Sung, Seoul (KR); Sang Hoon Han, Suwon-shi (KR); Han Kon Kim, Suwon-shi (KR); Hee Kyung Ju, Seoul (KR)

(73) Assignee: Amorepacific Corporation, Seoul (KR)

(*) Notice: Subject to any disclaimer, the term of this patent is extended or adjusted under 35 U.S.C. 154(b) by 1136 days.

(21) Appl. No.: 11/443,271

(22) Filed: May 31, 2006

(65) Prior Publication Data

US 2006/0216261 A1 Sep. 28, 2006

Related U.S. Application Data

(62) Division of application No. 10/336,024, filed on Jan. 3, 2003, now abandoned.

(30) Foreign Application Priority Data

| Jan. 5, 2002 | (KR) | 2002-613 |
| Jan. 5, 2002 | (KR) | 2002-614 |
| Apr. 8, 2002 | (KR) | 2002-19032 |
| May 27, 2002 | (KR) | 2002-29179 |

(51) Int. Cl.
| *A01N 43/04* | (2006.01) |
| *A01N 65/00* | (2009.01) |
| *A61K 31/70* | (2006.01) |
| *A61K 36/254* | (2006.01) |
| *A61K 36/258* | (2006.01) |

(52) U.S. Cl. ............... 514/25; 514/23; 424/728
(58) Field of Classification Search ............ 514/23, 514/25; 424/728

See application file for complete search history.

(56) References Cited

U.S. PATENT DOCUMENTS

| 5,118,671 A | 6/1992 | Bombardelli et al. |
| 5,147,859 A | 9/1992 | Bombardelli et al. |
| 5,166,139 A | 11/1992 | Bombardelli et al. |
| 5,576,016 A | 11/1996 | Amselem et al. |
| 5,663,160 A | 9/1997 | Meybeck et al. |
| 5,919,770 A | 7/1999 | Hideo et al. |
| 2003/0104079 A1* | 6/2003 | Sakanaka et al. ............ 424/728 |

FOREIGN PATENT DOCUMENTS

| EP | 0 283 713 A | 9/1988 |
| JP | 63-277691 | 11/1988 |
| JP | 1993-032522 | 2/1993 |
| JP | 1996-127526 | 5/1996 |
| WO | WO 93-18752 | 9/1993 |
| WO | WO 97 31013 A | 8/1997 |
| WO | WO 01 92289 A | 12/2001 |

OTHER PUBLICATIONS

Chang, I.-M. (Apr. 2001) Anti-aging and Health-promoting Constituents Derived from Traditional Oriental Herbal Remedies. Annals of the New York Academy of Sciences, vol. 928, Issue: Healthy Aging for Functional Longevity: Molecular and Cellular Interactions in Senscence, p. 281-286.*
Hasegawa, H., Sung, J.-H., Matsumiya, S., Uchiyama, M. (1996) Main Ginseng Saponin Metabolites Formed by Intestinal Bacteria. Planta Medica, vol. 62, p. 453-457.*
Atopkina et al "Cytotoxicity of Natural Ginseng Glycosides and Semisynthetic Analogues" 1999, Planta Medica. 65(1), 30-4.
Chemical Pharmaceutical Bulletin, 1983, 31(10), pp. 3691-3697.
Fitoterapia, 1986, 57(1), pp. 15-28.
Fitoterapia, 1986, 57(4), pp. 217-222.
Gezzi et al, "Dermocosmetic activity of ginsenosides. Note II: Instrumental evaluation of cutaneous hydration and elasticity", FITOTERAPIA 1986 Italy, vol. 57, No. 1, 1986, pp. 15-28; XP002237788.
Curri et al, "Dermocosmetic activity of ginsenosides. Note III: Long term evaluation of the moisturizing and tonifying effect on the face skin", FITOTERAPIA 1986 Italy, vol. 57, No. 4, 1986, pp. 217-222; XP002237789.

* cited by examiner

*Primary Examiner* — Scarlett Goon
(74) *Attorney, Agent, or Firm* — Nixon & Vanderhye P.C.

(57) ABSTRACT

Disclosed herein is nanoemulsion prepared by emulsifying main metabolites of ginseng saponin obtained by conversion of glucose, i.e. compound K (20-O-β-D-glucopyranosyl-20 (S)-protopanaxadiol), ginsenoside F1 (20-O-β-D-glucopyranosyl-20(S)-protopanaxatriol) and compound Y (20-O-[α-L-arabinopyranosyl(1→6)-β-D-glucopyranosyl]-20(S)-protopanaxadiol); and admixture thereof, in fine emulsion or liposome with dermotropic emulsifier by nano-emulsification; and having enhanced skin penetration, so to be effective in promoting proliferation of fibroblast and biosynthesis of collagen.

3 Claims, 3 Drawing Sheets

NANOEMULSION COMPRISING METABOLITES OF GINSENG SAPONIN AS AN ACTIVE COMPONENT AND A METHOD FOR PREPARING THE SAME, AND A SKIN-CARE COMPOSITION FOR ANTI-AGING CONTAINING THE SAME

CROSS REFERENCE TO RELATED APPLICATION

This application is a divisional of application Ser. No. 10/336,024 filed Jan. 3, 2003 now abandoned which in turn claims priority of Republic of Korea application Serial Nos. 2002-613 filed Jan. 5, 2002; 2002-614, filed Jan. 5, 2002; 2002-19032 filed Apr. 8, 2002; and 2002-29179 filed May 27, 2002, the entire content of each of which is hereby incorporated by reference in this application.

BACKGROUND OF THE INVENTION

1. Field of the Invention

The present invention relates to nanoemulsion comprising metabolites of ginseng saponin as an effective component and to a method for preparing the same, and to a skin-care composition for anti-aging containing the same. More particularly, the present invention relates to nanoemulsion comprising main metabolites of ginseng saponin obtained by conversion of glucose in the saponin, i.e. 20-O-β-D-glucopyranosyl-20(S)-protopanaxadiol, called "compound K" (hereinafter, "compound K"), 20-O-β-D-glucopyranosyl-20(S)-protopanaxatriol, called "ginsenoside F1" (hereinafter, "ginsenoside F1") and 20-O-[α-L-arabinopyranosyl(1→6)-β-D-glucopyranosyl]-20(S)-protopanaxadiol, called "compound Y" (hereinafter, "compound Y"), and admixture thereof. The present nanoemulsion may be prepared by emulsifying metabolites of ginseng saponin in fine emulsion or liposome with dermotropic emulsifier such as lecithin, by nano-emulsification such as high pressure homogenization and solvent extraction. The present nanoemulsion has enhanced skin penetration and thereby the cosmetic composition containing the same can promote proliferation of fibroblast and biosynthesis of collagen, so as to effectively prevent skin aging.

2. Description of Prior Art

Generally, skin is the first protective barrier against the surrounding environments such as change of temperature or humidity, UV and contaminants, and plays an important role in maintaining homeostasis such as thermoregulation. However, the skin may be damaged by excessive physical or chemical irritations, stress or sub-alimentation, resulting in losing normal functions and elasticity or so, to cause keratinization and to form wrinkles. On this, in order to prevent skin aging and to maintain healthy and elastic skin, a lot of efforts have been made to develop cosmetics containing biologically active materials obtained from animals, plants or microorganisms that play a role in maintaining skin functions and in activating skin cells, resulting in effectively controlling skin aging.

However, these active materials have some drawbacks such as insufficient efficacy or side effects such as skin irritation.

Accordingly, much researches has been made in order to provide cosmetic materials for anti-aging without skin irritation. Specially, many concerns on the extracts of ginseng led to extensive studies. These studies have widely focused on ginseng extracts, i.e. ginseng saponins and the intestinal flora metabolites thereof, which are obtained by isolation and conversion of glucose (via acid or alkaline hydrolysis or enzyme reaction), for example, compound K, ginsenoside F1 and compound Y.

Ginseng saponin has a specific chemical structure in which sugar such as glucose, rhamnose, xylose or arabinose is linked via ether bond to $R_1$, $R_2$ or $R_3$ positioned-alcoholic OH of aglycon of triterpene, a family of dammarane. Up to date, in total 29 kinds of saponins have been identified. Shibata, in 1964, called each component of said ginseng saponin "ginsenoside", which refers to glycoside contained in ginseng. Ginsenosides are classified into ginsenoside-Ro which is a family of oleanane saponin, and ginsenoside-Ra, -Rb1, -Rb2, -Rc, -Rd, -Re, -Rf, -Rg1, -Rg2, -Rg3 and -Rh according to the developing orders on TLC (thin-layer chromatography).

These ginseng saponins were found to be completely different from those found in about 750 other kinds of herbs in viewpoint of chemical structure and medical activity. Especially, ginseng saponins were revealed to have mild medicinal property and no toxicity or little hemolysis with excessive administration.

Further, it was reported that ginseng saponin applied on the skin in the form of liposome, which is a complex with phospholipid, has effects on imparting vitality to aged skin, increasing elasticity and hydration of the skin and accelerating blood circulation of the skin. (Curri. S B, Gezz, Z, Longhi, M G, Castelpietra, R: Fitoterapia, 57, 217(1986); Gezzi, A, Longhi, M G, Mazzoleni, R, Curri, S B: Fitoterapia, 57, 15(1986); Bombardelli, E. Curri, S B, Gariboldi, P L: Proc. 5th Intl. Ginseng Sym. Seoul Korea, 11(1988))

Thereafter, in order to apply ginseng saponin as an anti-aging material, ginseng aglycon was bioconverted for enhancing skin penetration and tested for the efficacy on the skin, which was confirmed as the same as that of ginseng saponin.

As for the applications of ginseng extracts or saponins, U.S. Pat. Nos. 5,565,207, 5,567,419, 5,578,312, 5,663,160, 5,626,868, 5,753,242, 5,747,300, 5,853,705, 6,027,728, 6,063,366, 6,221,372 and 6,228,378 disclosed cosmetic compositions and U.S. Pat. Nos. 5,569,459, 5,571,516, 5,587,167, 5,674,488, 5,665,393, 5,629,316, 5,776,460, 5,739,165, 5,916,555, 6,071,521, 6,083,512 and 6,255,313 disclosed pharmaceutical compositions. In addition, U.S. Pat. Nos. 5,591,611, 5,591,612, 5,736,380, 5,789,392, 5,780,620, 5,922,580, 5,935,636, 6,132,726, 6,156,817 and 6,207,164 disclosed methods for isolation and purification of ginseng saponins.

However, ginseng saponin is extremely hydrophilic and has high molecular weight due to its chemical structure in which sugar is linked via ether bond to $R_1$, $R_2$ or $R_3$ positioned-alcoholic OH of dammarane aglycon, thereby interfering with penetration into stratum corneum and absorption into inner dermis.

While, extensive studies on saponin metabolites revealed that the efficacy of ginseng saponin is due to the metabolites decomposed by human intestinal bacteria, not due to saponin itself. For example, ginsenoside-Rh1, Rh2 and F1, compound K and others with one glucose linked to aglycon of saponin have been reported to have pharmacological effects such as inhibitions of proliferations of cancerous cells and tumors, and enlargement of activities of anticancer agents.

Nevertheless, methods for application onto the skin and formulation of the compound K, ginsenoside F1 and compound Y obtained by removing a part of sugar moiety from ginseng saponin have not been researched yet.

Under these circumstances, in order to find a method for application of the compound K, ginsenoside F1 and compound Y onto the skin, the present inventors have conducted extensive studies on micro- and nano-emulsification. As a result thereof, the inventors found that nanoemulsion, obtained by emulsifying metabolites of ginseng saponin in fine emulsion or liposome with dermotropic emulsifier by nano-emulsification, has enhanced skin penetration and thereby can be applied to skin-care compositions for anti-aging. The present cosmetic composition containing the nanoemulsion can promote proliferation of fibroblast and biosynthesis of collagen, so to effectively prevent skin aging.

SUMMARY OF THE INVENTION

Therefore, an object of the invention is to provide a nanoemulsion comprising metabolites of ginseng saponin and having enhanced skin penetration.

Further, another object of the present invention is to provide a method for preparing the nanoemulsion.

A further object of the present invention is to provide a skin-care composition for anti-aging containing the nanoemulsion, which can promote fibroblast-proliferation and collagen-biosynthesis.

The nanoemulsion of the present invention comprises main metabolites of ginseng saponin obtained by conversion of glucose, i.e. compound K, ginsenoside F1, compound Y, or admixture thereof. The present nanoemulsion may be prepared by emulsifying metabolites of ginseng saponin in fine emulsion or liposome with dermotropic emulsifier by nano-emulsification. The present nanoemulsion has enhanced skin penetration and thereby the cosmetic composition containing the same can promote proliferation of fibroblast and biosynthesis of collagen, so to effectively prevent skin aging.

These and other objects and advantages of the invention will become apparent to those skilled in the art from the following detailed description with reference to the accompanying drawings.

DETAILED DESCRIPTION OF THE INVENTION

Figure 1:
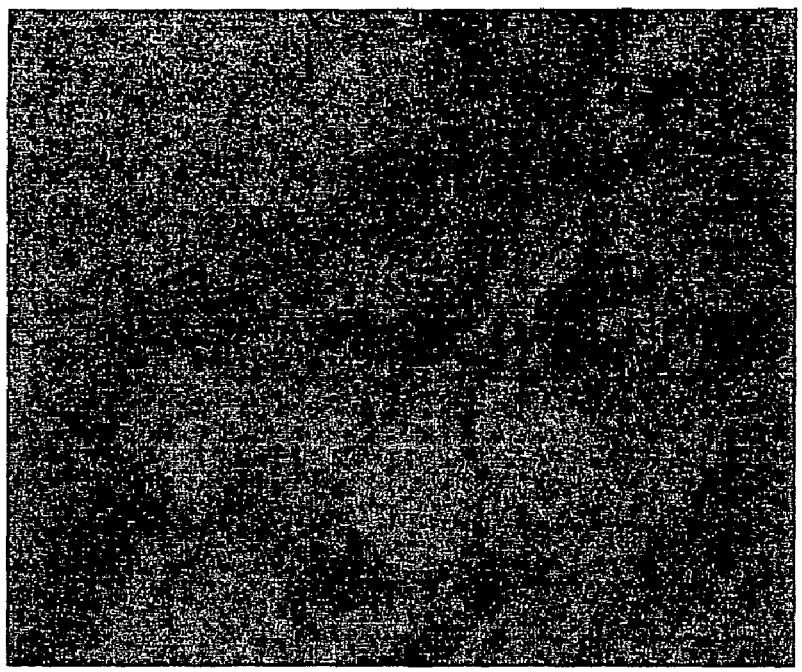
FIG. 1 is a structural photograph of epidermal cells showing the effect of Formulation 7 on biosynthesis of collagen.

The following is a detailed description of the present invention.

The present invention relates to nanoemulsion comprising, as an effective component, metabolites of ginseng saponin obtained by conversion of glucose (via acid or alkaline hydrolysis or enzyme reaction). The present nanoemulsion of the present invention comprises at least on selected from the group consisting of compound K (20-O-β-D-glucopyranosyl-20(S)-protopanaxadiol), ginsenoside F1 (20-O-β-D-glucopyranosyl-20(S)-protopanaxatriol), compound Y (20-O-[α-L-arabinopyranosyl(1-6)-β-D-glucopyranosyl]-20(S)-protopanaxadiol) and admixture thereof.

Hereinafter, the above admixture of metabolites that comprising compound K, ginsenoside F1 and compound Y as main components is called as "Bio GF1K". In the present invention, Bio GF1K may be preferable in that it may not need further purification into each metabolite. More particularly, Bio GF1K may be admixture of metabolites obtained by conversion of glucose (via acid or alkaline hydrolysis or enzyme reaction) from purified ginseng saponin, comprising 30-50 wt % of compound K, 5~25 wt % of ginsenoside F1 and 5~25 wt % of compound Y.

The present nanoemulsion may be prepared by emulsifying metabolites of ginseng saponin into fine emulsion or liposome, using nano-emulsification. More particularly, the present nanoemulsion may be prepared by emulsifying metabolites of ginseng saponin into fine emulsion or liposome with dermotropic emulsifier such as lecithin or its derivatives, by nano-emulsification such as homogenization or solvent extraction. The obtained nanoemulsion has enhanced skin penetration and thereby the skin-care composition containing the same can promote proliferation of fibroblast and biosynthesis of collagen, so as to be superior in preventing skin aging.

Said compound K is represented by the following formula 1:

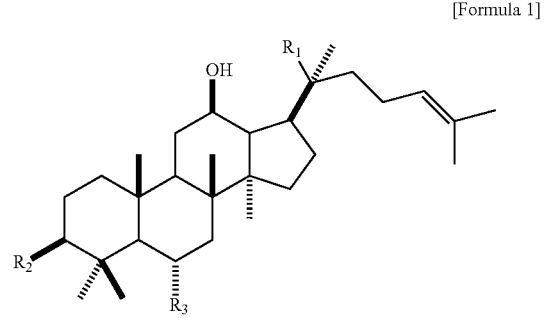

[Formula 1]

(wherein, $R_1$ is O-Glc, $R_2$ is OH and $R_3$ is H).

Said ginsenoside F1 is represented by the following formula 2:

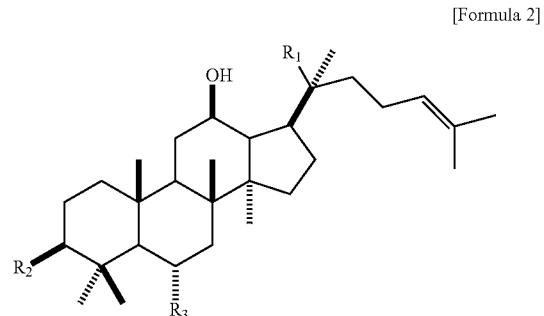

[Formula 2]

(wherein, $R_1$ is O-Glc, $R_2$ is OH and $R_3$ is OH).

Said compound Y is represented by the following formula 3

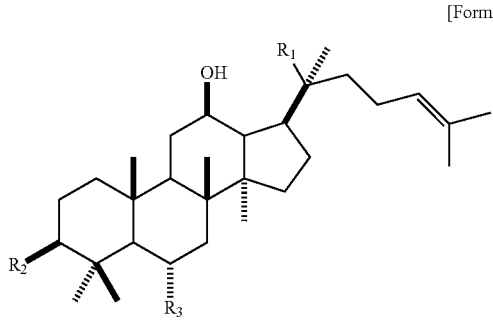

[Formula 3]

(wherein, $R_1$ is O-Glc$^6$-$^1$Arap, $R_2$ is OH and $R_3$ is H).

Preferably, said Bio GF1K comprises 30~50 wt % of compound K represented by the formula 1, 5~25 wt % of ginsenoside F1 represented by the formula 2 and 5~25 wt % of compound Y represented by the formula 3 as main components.

In general, hydrophobic material is more effective in skin penetration than hydrophilic one. This is because of intercellular lipids such as ceramide distributed in stratum corneum of the epidermis. Hydrophobic material has reciprocity with intercellular lipids, thereby passing through the outermost layer of the epidermis more easily. As the above formula 1 to 3 show, said compound K, gensenoside F1 and compound Y have reduced molecular weight and are hydrophobic by removing a part of sugar moiety from ginseng saponin, resulting in enhancement of skin penetration.

In the present invention, Bio GF1K may be prepared by removing a part of sugar moiety from ginseng saponin via acid or alkaline hydrolysis or enzyme reaction and then by passing through silica gel column. Further, Bio GF1K may be fractionated by changing the polarity of eluent on silica gel column and then separated into each metabolite of ginseng saponin on TLC.

An enzyme employed in the present invention may be β-glucosidase, which hydrolyzes sugar bond linked to saponin; α,β-arabinosidase, α,β-rhamnosidase, which hydrolyze exo sugar; and enzyme complex thereof.

Metabolites of ginseng saponin may be incorporated into the present nanoemulsion in an amount of $10^{-10}$~50% by weight based on the total weight of nanoemulsion. More preferably, metabolites may be incorporated in an amount of 0.001~30 wt %.

Further, the present nanoemulsion may be incorporated into a skin-care composition in an amount of $10^{-10}$~50% by weight based on the total weight of composition, depending on a method of preparation thereof. If the amount is less than $10^{-10}$ wt %, it may be difficult to obtain the aimed effect. While, if the amount is more than 50 wt %, there may be a problem in stability of formulation.

The present nanoemulsion may have the diameter of 30~500 nm, more preferably 50~300 nm. As a result, the present nanoemulsion can increase a surface contacting with the skin in comparison with conventional emulsion having the diameter of 500 nm or more and thereby can increase area for skin penetration. Additionally, in consideration that gap-size of intercellular lipids in stratum corneum is about 50 nm and that emulsified film of emulsion is soft and flexible, the present nanoemulsion can be easily absorbed and spread into intercellular lipids. That is, through two routes, one of which is increased contact surface with the skin and the other of which is increased permeation and spread into intercellular lipids, the present nanoemulsion having the diameter of 30~500 nm obtained by nano-emulsification can enhance skin penetration thereof and of metabolites contained therein as an effective component.

Further, a lecithin employed in the present invention as an emulsifier is liposome containing one or more selected from the group consisting of unsaturated choline compound such as phosphatidylcholine and lysophosphatidylcholine; serine compound; cephalin compound such as phosphatidylethanolamine; and hydrogenated compound thereof. It may be employed in an amount of 0.5~10%, more preferably 2~5% by weight based on the total weight of nanoemulsion.

Further, supplementary emulsifier such as anionic, cationic, nonionic or amphoteric emulsifier may be employed together with lecithin in a ratio of 0.5~5 times, more preferably 1~3 times based on the weight of lecithin.

In addition, as a nano-emulsification, homogenization (under 500~2,500 bar) or solvent extraction may be employed.

The obtained nanoemulsion may be incorporated into a skin-care composition for anti-aging. The present composition may be formulated, but not limited thereto, into cosmetic composition such as skin softeners, astringents, nutrient toilet water, nutrient creams, massage creams, essences, eye creams, eye essences, cleansing creams, cleansing foams, cleansing water, packs, powders, body lotions, body creams, body oils, body essences, make-up bases, foundation, hairdyes, shampoos, rinses, body cleansers, toothpastes and oral cleaning fluid; and pharmaceutical composition such as lotions, ointments, gels, creams, patches and sprays. Also, the composition may further incorporate other ingredients depending on the formulation or the final purposes thereof.

PREFERRED EMBODIMENT OF THE INVENTION

The present invention will be described in more detail by way of the following examples, which should not be considered to limit the scope of the present invention.

Reference Example 1

Preparation of Purified Ginseng Saponin

To 2 kg of red ginseng, 4 l of distilled water and ethanol containing water were added and then refluxed three (3) times. The crude extract was settled down at a temperature of 15° C. for 6 days, and then filtered and centrifuged to remove residue. After, the filtrate (extract) was concentrated under reduced pressure. The concentrated extract was suspended in water and then extracted with 1 l of ether five (5) times to remove pigment. The aqueous part was extracted with 500 ml of 1-butanol three (3) times. All the 1-butanol parts were treated with 5% KOH and washed with distilled water, and then concentrated under reduced pressure to obtain 1-butanol extract. The extract was dissolved in a small quantity of methanol and added to a large quantity of ethylacetate. The obtained precipitate was dried, to give 100 g (yield: 5%) of purified ginseng saponin.

Reference Example 2

Preparation of Bio GF1K Via Acid Hydrolysis

To 10 g of purified ginseng saponin obtained in Reference Example 1, twenty (20) times (v/w) of 7% sulfuric acid/50% ethanol (v/w) mixture was added, and then refluxed in 100° C. of water bath for 6 hours to hydrolyze sugar-bond linked to ginseng saponin. The reaction mixture was concentrated under reduced pressure to remove solvent. The residue was suspended in 1,000 ml of distilled water and then extracted with same quantity of ether three (3) times. All the ether parts were washed with distilled water, dehydrated over magnesium sulfate anhydride ($MgSO_4$), filtered and then concentrated, to give crude product. The crude product was fractionated on silica gel column chromatography (as an eluent, chloroform:methanol=9:1→4:1), to give 210 mg (yield: 2%) of Bio GF1K comprising 70 mg of compound K, 30 mg of ginsenoside F1 and 35 mg of compound Y as main components.

Further, each fraction was subjected to thin-layer chromatography (chloroform/methanol/distilled water=65/35/10), to give 70 mg of compound K (Rf=0.73), 30 mg of ginsenoside F1 (Rf=0.65) and 35 mg of compound Y (Rf=0.49).

Reference Example 3

Preparation of Bio GF1K Via Alkaline Hydrolysis 10 g of purified ginseng saponin obtained in Reference Example 1 was dissolved in 500 ml of dried pyridine. Thereto was added sodium methoxide (powder, 10 g) and then refluxed in oil bath for 8 hours, to hydrolyze sugar-bond linked to ginseng saponin. The reaction mixture was concentrated under reduced pressure to remove solvent. The residue was suspended in 1,000 ml of distilled water and then extracted with same quantity of ether three (3) times. All the ether parts were washed with distilled water, dehydrated over magnesium sulfate anhydride ($MgSO_4$), filtered and then concentrated, to give crude product. The crude product was fractionated on silica gel column chromatography (as an eluent, chloroform:methanol=9:1→4:1), to give 205 mg (yield: 2%) of Bio GF1K comprising 75 mg of compound K, 35 mg of ginsenoside F1 and 30 mg of compound Y.

Then, each fraction was subjected to thin-layer chromatography (chloroform/methanol/distilled water=65/35/10), to give 75 mg of compound K (Rf=0.73), 35 mg of ginsenoside F1 (Rf=0.65) and 30 mg of compound Y (Rf=0.49).

Reference Example 4-1

Preparation of Bio GF1K Via Enzyme Reaction 10 g of purified ginseng saponin obtained in Reference Example 1 was dissolved in 100 l of citrate buffer (pH 5.5). Thereto was added 1 g of naringinase separated from *Penicillium* and then stirred in 40° C. of water bath for 48 hours. The reaction was checked periodically on TLC (thin-layer chromatography). When the substrate was completely consumed, the reaction was terminated by heating in hot water for 10 minutes. The reaction mixture was extracted with same quantity of ether three (3) times, and then concentrated. The obtained product was fractionated on silica gel column chromatography (as an eluent, chloroform:methanol=9:1→4:1), to give 1,050 mg (yield: 10.5%) of Bio GF1K comprising 440 mg of compound K, 150 mg of ginsenoside F1 and 140 mg of compound Y (Rf=0.49).

Then, each fraction was subjected to thin-layer chromatography (chloroform/methanol/distilled water-65/35/10), to give 440 mg of compound K (Rf=0.73), 150 mg of ginsenoside F1 (Rf=0.65) and 140 mg of compound Y (Rf=0.49).

In addition, the following enzyme reactions may be utilized for the preparation of the present Bio GF1K.

Reference Example 4-2

10 g of purified ginseng saponin was dissolved in 100 ml of citrate buffer containing 15% ethanol (pH 4.0). Thereto was added 0.5 g of *naringinase* separated from *Penicillium* and then stirred in 40° C. of water bath for 48 hours. The reaction was checked periodically on TLC (thin-layer chromatography). When the substrate was completely consumed, the reaction was terminated by heating in hot water for 10 minutes. The reaction mixture was extracted with same quantity of ethyl acetate three (3) times, and then concentrated.

The obtained product was fractionated on silica gel column chromatography (as an eluent, chloroform:methanol=9:1→4:1), to give 373 mg (yield: 3.73%) of Bio GF1K comprising 150 mg of compound K, 100 mg of ginsenoside F1 and 102 mg of compound Y.

Then each fraction was subjected to thin-layer chromatography (chloroform/methanol/distilled water=65/35/10), to give 150 mg of compound K (Rf=0.73), 100 mg of ginsenoside F1 (Rf=0.65) and 102 mg of compound Y (Rf=0.49).

Reference Example 4-3

10 g of purified ginseng saponin was dissolved in 100 ml of citrate buffer containing 15% ethanol (pH 4.0). Thereto was added 2 g of pectinase separated from *Aspergillus* and then stirred in 30° C. of water bath for 48 hours. The reaction was checked periodically on TLC (thin-layer chromatography). When the substrate was completely consumed, the reaction was terminated by heating in hot water for 10 minutes. The reaction mixture was extracted with same quantity of ethyl acetate three (3) times, and then concentrated. The obtained product was fractionated on silica gel column chromatography (as an eluent, chloroform:methanol=9:1→4:1), to give 190 mg (yield: 1.9%) of Bio GF1K comprising 80 mg of compound K, 30 mg of ginsenoside F1 and 35 mg of compound Y.

Then, each fraction was subjected to thin-layer chromatography (chloroform/methanol/distilled water=65/35/10), to give 80 mg of compound K (Rf=0.73), 30 mg of ginsenoside F1 (Rf=0.65) and 35 mg of compound Y (Rf=0.49).

Reference Example 4-4

10 g of purified ginseng saponin was dissolved in 100 ml of citrate buffer (pH 5.5). Thereto was added 2 g of pectinase separated from *Aspergillus* and then stirred in 30° C. of water bath for 48 hours. The reaction was checked periodically on TLC (thin-layer chromatography). When the substrate was completely consumed, the reaction was terminated by heating in hot water for 10 minutes. The reaction mixture was extracted with same quantity of ether three (3) times, and then concentrated. The obtained product was fractionated on silica gel column chromatography (as an eluent, chloroform:methanol=9:1→4:1), to give 493 mg (yield: 4.93%) of Bio GF1K comprising 180 mg of compound K, 82 mg of ginsenoside F1 and 85 mg of compound Y.

Then, each fraction was subjected to thin-layer chromatography (chloroform/methanol/distilled water=65/35/10), to give 180 mg of compound K (Rf=0.73), 82 mg of ginsenoside F1 (Rf=0.65) and 85 mg of compound Y (Rf=0.49).

In the following Examples 1~6, the present nanoemulsions were prepared by comprising said compound K, ginsenoside F1 and compound Y obtained in said Reference Examples. Each ingredient and its amount are specified in Table 1.

Example 1

Bio GF1K comprising compound K, ginsenoside F1 and compound Y was added to the solution containing lecithin, hydrogenated lecithin, cholesterol, soy oil and propylene glycol, and then heated to a temperature of 70~75° C. to be completely dissolved. Then, it was mixed with pre-heated aqueous parts (distilled water, EDTA) and pre-emulsified under 3,000~6,000 rpm for 3 minutes with general homomixer. Subsequently, it was emulsified under 1,000 Bar/3 cycles with Microfluidizer.

Among said ingredients, hydrogenated lecithin has good emulsion-stabilizing efficiency. But, it is an inferior dermotropic to unsaturated lecithin and thereby exhibits poor skin penetration. Therefore, in this example, two kinds of lecithin were admixed.

Example 2

The procedure described in Example 1 was followed by using compound K instead of Bio GF1K.

Example 3

The procedure described in Example 1 was followed by using ginsenoside F1, instead of Bio GF1K.

Example 4

The procedure described in Example 1 was followed by using compound Y, instead of Bio GF1K.

Example 5

Lecithin, PEG-5 grapeseed sterol, capric/caprylic triglyceride, BHT, α-tocopherol and pentylene glycol were dissolved in ethanol. Thereto was added Bio GF1K and then heated to a temperature of 70~75° C. to be completely dissolved. Then, it was mixed with pre-heated aqueous parts (distilled water, EDTA) and pre-emulsified under 3,000~6,000 rpm for 3 minutes with general homomixer. Subsequently, it was emulsified under 1,000 Bar/3 cycles with Microfluidizer.

Among said ingredients, BHT as an antioxidant was added in order to complement chemical instability of unsaturated lecithin. Further, PEG-5 grapeseed sterol as a supplementary emulsifier was added in order to increase emulsion-stability.

Example 6

Hydrogenated lecithin, hydrogenated lysophosphatidyl choline (HLPC) and propylene glycol were dissolved in ethanol. Thereto was added Bio GF1K and then heated to a temperature of 70~75° C. to be completely dissolved. Then, it was mixed with pre-heated aqueous parts (distilled water, EDTA, glycerin, betain) and pre-emulsified under 3,000~6,000 rpm for 3 minutes with general homomixer. Subsequently, it was emulsified under 1,000 Bar/3 cycles with Microfluidizer.

Among said ingredients, hydrogenated lysophosphatidyl choline (HLPC) is obtained by hydrolyzing hydrogenated phosphatidyl choline (HPC) which constitutes hydrogenated lecithin. It is superior to HPC in emulsibility.

In order to compare the nanoemulsion obtained in Examples 1~6 with purified ginseng saponin in skin penetration, Comparative Examples 1~3 were prepared by comprising purified ginseng saponin and the ingredients specified in Table 1.

Comparative Example 1

The procedure described in Example 1 was followed by emulsifying purified ginseng saponin prepared by Reference Example 1, instead of emulsifying Bio GF1K.

Comparative Example 2

The procedure described in Example 5 was followed by emulsifying purified ginseng saponin prepared by Reference Example 1, instead of emulsifying Bio GF1K.

Comparative Example 3

The procedure described in Example 6 was followed by emulsifying purified ginseng saponin prepared by Reference Example 1, instead of emulsifying Bio GF1K.

Example 7

The procedure described in Example 5 was followed by using compound K instead of Bio GF1K.

Example 8

The procedure described in Example 5 was followed by using ginsenoside F1, instead of Bio GF1K.

Example 9

The procedure described in Example 5 was followed by using compound Y, instead of Bio GF1K.

Example 10

The procedure described in Example 6 was followed by using compound K instead of Bio GF1K.

Example 11

The procedure described in Example 6 was followed by using ginsenoside F1, instead of Bio GF1K.

Example 12

The procedure described in Example 6 was followed by using compound Y, instead of Bio GF1K.

The above examples 7 to 12 are not shown in the table 1.

TABLE 1

(Unit: wt %)

| Ingredients | Examples | | | | | | C. Examples | | |
|---|---|---|---|---|---|---|---|---|---|
| | 1 | 2 | 3 | 4 | 5 | 6 | 1 | 2 | 3 |
| Hydrogenated lecithin | 1.5 | 1.5 | 1.5 | 1.5 | — | 2.5 | 1.5 | — | 2.5 |
| Lecithin | 3.0 | 3.0 | 3.0 | 3.0 | 2.0 | — | 3.0 | 2.0 | — |
| PEG-5 grapeseed sterol | — | — | — | — | 4.0 | — | — | 4.0 | — |
| Capric/caprylic triglyceride | — | — | — | — | 7.5 | — | — | 7.5 | — |
| Hydrogenated lysophosphatidyl | — | — | — | — | — | 0.15 | — | — | 0.15 |
| Cholesterol | 1.5 | 1.5 | 1.5 | 1.5 | — | — | 1.5 | — | — |
| Soy oil | 7.5 | 7.5 | 7.5 | 7.5 | — | — | 7.5 | — | — |
| Pentylene glycol | — | — | — | — | 5.0 | — | — | 5.0 | — |
| Propylene glycol | 5.0 | 5.0 | 5.0 | 5.0 | — | 4.0 | 5.0 | — | 4.0 |
| Ethanol | — | — | — | — | 7.5 | 6.5 | — | 7.5 | 6.5 |
| Bio GF1K | 1.5 | — | — | — | 1.5 | 1.5 | — | — | — |
| Compound K | — | 1.5 | — | — | — | — | — | — | — |
| Ginsenoside F1 | — | — | 1.5 | — | — | — | — | — | — |
| Compound Y | — | — | — | 1.5 | — | — | — | — | — |
| Purified ginseng saponin | — | — | — | — | — | — | 1.5 | 1.5 | 1.5 |
| α-tocopherol | — | — | — | — | 0.2 | — | — | 0.2 | — |
| Butylated hydroxy toluene (BHT) | — | — | — | — | 0.01 | — | — | 0.01 | — |
| Distilled water | to | to | to | to | to | to | to | to | to |
| EDTA | 0.05 | 0.05 | 0.05 | 0.05 | 0.05 | 0.05 | 0.05 | 0.05 | 0.05 |
| Glycerin | — | — | — | — | — | 4.0 | — | — | 4.0 |
| Betain | — | — | — | — | — | 1.0 | — | — | 1.0 |

In addition, in order to confirm enhancement in skin penetration of nanoemulsion prepared by dermotropic emulsifier and nano-emulsification, Comparative Example 4 was prepared by dissolving 1.5 wt % of Bio GF1K obtained in Reference Example 4-1 in ethanol solution, Comparative Example 5 was prepared by dissolving 1.5 wt % of Bio GF1K in propylene glycol/ethanol solution and Comparative Example 6 was prepared by dissolving 1.5 wt % of Bio GF1K in pentylene glycol/ethanol solution.

Also, Comparative Example 7 was prepared by dissolving 1.5 wt % of purified ginseng saponin in ethanol solution, Comparative Example 8 was prepared by dissolving 1.5 wt % of purified ginseng saponin in propylene glycol/ethanol solution and Comparative Example 9 was prepared by dissolving 1.5 wt % of purified ginseng saponin in pentylene glycol/ethanol solution. C. Examples 4~9 are presented in Table 2.

TABLE 2

| | Ingredient | Amount | Diluent |
|---|---|---|---|
| C. Ex. 4 | Bio GF1K | 1.5 wt % | Ethanol |
| C. Ex. 5 | Bio GF1K | 1.5 wt % | Propylene glycol/Ethanol(4.0/6.5) |
| C. Ex. 6 | Bio GF1K | 1.5 wt % | Pentylene glycol/Ethanol(5.0/7.5) |
| C. Ex. 7 | Purified ginseng saponin | 1.5 wt % | Ethanol |
| C. Ex. 8 | Purified ginseng saponin | 1.5 wt % | Propylene glycol/Ethanol(4.0/6.5) |
| C. Ex. 9 | Purified ginseng saponin | 1.5 wt % | Pentylene glycol/Ethanol(5.0/7.5) |

In addition, the present nanoemulsion was formulated into the following skin-care compositions. In Tables 3~7, unit is wt %.

<Formulation: Cream>

TABLE 3

| Materials | Formulations | | | | | | C. Formulations | | |
|---|---|---|---|---|---|---|---|---|---|
| | 1 | 2 | 3 | 4 | 5 | 6 | 1 | 2 | 3 |
| Nanoemulsion of Ex. 1 | 10.0 | — | — | — | — | — | — | — | — |
| Nanoemulsion of Ex. 2 | — | 10.0 | — | — | — | — | — | — | — |
| Nanoemulsion of Ex. 3 | — | — | 10.0 | — | — | — | — | — | — |
| Nanoemulsion of Ex. 4 | — | — | — | 10.0 | — | — | — | — | — |
| Nanoemulsion of Ex. 5 | — | — | — | — | 10.0 | — | — | — | — |
| Nanoemulsion of Ex. 6 | — | — | — | — | — | 10.0 | — | — | — |
| Nanoemulsion of C. Ex. 1 | — | — | — | — | — | — | 10.0 | — | — |
| Nanoemulsion of C. Ex. 2 | — | — | — | — | — | — | — | 10.0 | — |
| Nanoemulsion of C. Ex. 3 | — | — | — | — | — | — | — | — | 10.0 |
| Beeswax | 10.0 | 10.0 | 10.0 | 10.0 | 10.0 | 10.0 | 10.0 | 10.0 | 10.0 |
| Polysorbate-60 | 1.5 | 1.5 | 1.5 | 1.5 | 1.5 | 1.5 | 1.5 | 1.5 | 1.5 |
| Sorbitan sesquioleate | 0.5 | 0.5 | 0.5 | 0.5 | 0.5 | 0.5 | 0.5 | 0.5 | 0.5 |
| PEG-60 hydrogenated castor oil | 2.0 | 2.0 | 2.0 | 2.0 | 2.0 | 2.0 | 2.0 | 2.0 | 2.0 |
| Liquid paraffin | 10.0 | 10.0 | 10.0 | 10.0 | 10.0 | 10.0 | 10.0 | 10.0 | 10.0 |
| Squalane | 5.0 | 5.0 | 5.0 | 5.0 | 5.0 | 5.0 | 5.0 | 5.0 | 5.0 |
| Capric/caprylic triglyceride | 5.0 | 5.0 | 5.0 | 5.0 | 5.0 | 5.0 | 5.0 | 5.0 | 5.0 |
| Glycerin | 5.0 | 5.0 | 5.0 | 5.0 | 5.0 | 5.0 | 5.0 | 5.0 | 5.0 |
| Butylene glycol | 3.0 | 3.0 | 3.0 | 3.0 | 3.0 | 3.0 | 3.0 | 3.0 | 3.0 |
| Propylene glycol | 3.0 | 3.0 | 3.0 | 3.0 | 3.0 | 3.0 | 3.0 | 3.0 | 3.0 |

TABLE 3-continued

|  | Formulations | | | | | | C. Formulations | | |
|---|---|---|---|---|---|---|---|---|---|
| Materials | 1 | 2 | 3 | 4 | 5 | 6 | 1 | 2 | 3 |
| Triethanolamine | 0.2 | 0.2 | 0.2 | 0.2 | 0.2 | 0.2 | 0.2 | 0.2 | 0.2 |
| Preservative | q.s. | q.s. | q.s. | q.s. | q.s. | q.s. | q.s. | q.s. | q.s. |
| Pigments | q.s. | q.s. | q.s. | q.s. | q.s. | q.s. | q.s. | q.s. | q.s. |
| Perfume | q.s. | q.s. | q.s. | q.s. | q.s. | q.s. | q.s. | q.s. | q.s. |
| Distilled water | to 100 | to 100 | to 100 | to 100 | to 100 | to 100 | to 100 | to 100 | to 100 |

<Formulation: Nutrient Water>

TABLE 4

|  | Formulations | | | | | | C. Formulations | | |
|---|---|---|---|---|---|---|---|---|---|
| Materials | 7 | 8 | 9 | 10 | 11 | 12 | 4 | 5 | 6 |
| Nanoemulsion of Ex. 1 | 10.0 | — | — | — | — | — | — | — | — |
| Nanoemulsion of Ex. 2 | — | 10.0 | — | — | — | — | — | — | — |
| Nanoemulsion of Ex. 3 | — | — | 10.0 | — | — | — | — | — | — |
| Nanoemulsion of Ex. 4 | — | — | — | 10.0 | — | — | — | — | — |
| Nanoemulsion of Ex. 5 | — | — | — | — | 10.0 | — | — | — | — |
| Nanoemulsion of Ex. 6 | — | — | — | — | — | 10.0 | — | — | — |
| Nanoemulsion of C. Ex. 1 | — | — | — | — | — | — | 10.0 | — | — |
| Nanoemulsion of C. Ex. 2 | — | — | — | — | — | — | — | 10.0 | — |
| Nanoemulsion of C. Ex. 3 | — | — | — | — | — | — | — | — | 10.0 |
| Cetyl ethyl hexanoate | 5.0 | 5.0 | 5.0 | 5.0 | 5.0 | 5.0 | 5.0 | 5.0 | 5.0 |
| Cetostearyl alcohol | 1.0 | 1.0 | 1.0 | 1.0 | 1.0 | 1.0 | 1.0 | 1.0 | 1.0 |
| Lipophilic monostearic stearate | 0.8 | 0.8 | 0.8 | 0.8 | 0.8 | 0.8 | 0.8 | 0.8 | 0.8 |
| Squalane | 2.0 | 2.0 | 2.0 | 2.0 | 2.0 | 2.0 | 2.0 | 2.0 | 2.0 |
| Polysorbate-60 | 1.5 | 1.5 | 1.5 | 1.5 | 1.5 | 1.5 | 1.5 | 1.5 | 1.5 |
| Sorbitan sesquioleate | 0.5 | 0.5 | 0.5 | 0.5 | 0.5 | 0.5 | 0.5 | 0.5 | 0.5 |
| Glycerin | 5.0 | 5.0 | 5.0 | 5.0 | 5.0 | 5.0 | 5.0 | 5.0 | 5.0 |
| Triethanol amine | 0.2 | 0.2 | 0.2 | 0.2 | 0.2 | 0.2 | 0.2 | 0.2 | 0.2 |
| Carboxyvinyl polymer | 0.2 | 0.2 | 0.2 | 0.2 | 0.2 | 0.2 | 0.2 | 0.2 | 0.2 |
| Preservative | q.s. | q.s. | q.s. | q.s. | q.s. | q.s. | q.s. | q.s. | q.s. |
| Pigments | q.s. | q.s. | q.s. | q.s. | q.s. | q.s. | q.s. | q.s. | q.s. |
| Perfume | q.s. | q.s. | q.s. | q.s. | q.s. | q.s. | q.s. | q.s. | q.s. |
| Distilled water | to 100 | to 100 | to 100 | to 100 | to 100 | to 100 | to 100 | to 100 | to 100 |

<Formulation: Skin Softener>

TABLE 5

|  | Formulations | | | | | | C. Formulations | | |
|---|---|---|---|---|---|---|---|---|---|
| Materials | 13 | 14 | 15 | 16 | 17 | 18 | 7 | 8 | 9 |
| Nanoemulsion of Ex. 1 | 10.0 | — | — | — | — | — | — | — | — |
| Nanoemulsion of Ex. 2 | — | 10.0 | — | — | — | — | — | — | — |
| Nanoemulsion of Ex. 3 | — | — | 10.0 | — | — | — | — | — | — |
| Nanoemulsion of Ex. 4 | — | — | — | 10.0 | — | — | — | — | — |
| Nanoemulsion of Ex. 5 | — | — | — | — | 10.0 | — | — | — | — |
| Nanoemulsion of Ex. 6 | — | — | — | — | — | 10.0 | — | — | — |
| Nanoemulsion of C. Ex. 1 | — | — | — | — | — | — | 10.0 | — | — |
| Nanoemulsion of C. Ex. 2 | — | — | — | — | — | — | — | 10.0 | — |
| Nanoemulsion of C. Ex. 3 | — | — | — | — | — | — | — | — | 10.0 |
| Betain | 3.0 | 3.0 | 3.0 | 3.0 | 3.0 | 3.0 | 3.0 | 3.0 | 3.0 |
| Natogum | 3.0 | 3.0 | 3.0 | 3.0 | 3.0 | 3.0 | 3.0 | 3.0 | 3.0 |
| Cellulose gum | 0.08 | 0.08 | 0.08 | 0.08 | 0.08 | 0.08 | 0.08 | 0.08 | 0.08 |
| Ethanol | 5.0 | 5.0 | 5.0 | 5.0 | 5.0 | 5.0 | 5.0 | 5.0 | 5.0 |
| Polyoxyethylene hydrogenated castor oil | 0.5 | 0.5 | 0.5 | 0.5 | 0.5 | 0.5 | 0.5 | 0.5 | 0.5 |
| Tocopheryl acetate | 0.2 | 0.2 | 0.2 | 0.2 | 0.2 | 0.2 | 0.2 | 0.2 | 0.2 |
| Preservative | q.s. | q.s. | q.s. | q.s. | q.s. | q.s. | q.s. | q.s. | q.s. |
| Pigments | q.s. | q.s. | q.s. | q.s. | q.s. | q.s. | q.s. | q.s. | q.s. |
| Distilled water | to 100 | to 100 | to 100 | to 100 | to 100 | to 100 | to 100 | to 100 | to 100 |

<Formulation: Gel>

TABLE 6

| Materials | Formulations | | | | | | C. Formulations | | |
|---|---|---|---|---|---|---|---|---|---|
| | 19 | 20 | 21 | 22 | 23 | 24 | 10 | 11 | 12 |
| Nanoemulsion of Ex. 1 | 10.0 | — | — | — | — | — | — | — | — |
| Nanoemulsion of Ex. 2 | — | 10.0 | — | — | — | — | — | — | — |
| Nanoemulsion of Ex. 3 | — | — | 10.0 | — | — | — | — | — | — |
| Nanoemulsion of Ex. 4 | — | — | — | 10.0 | — | — | — | — | — |
| Nanoemulsion of Ex. 5 | — | — | — | — | 10.0 | — | — | — | — |
| Nanoemulsion of Ex. 6 | — | — | — | — | — | 10.0 | — | — | — |
| Nanoemulsion of C. Ex. 1 | — | — | — | — | — | — | 10.0 | — | — |
| Nanoemulsion of C. Ex. 2 | — | — | — | — | — | — | — | 10.0 | — |
| Nanoemulsion of C. Ex. 3 | — | — | — | — | — | — | — | — | 10.0 |
| EDTA.2Na | 0.02 | 0.02 | 0.02 | 0.02 | 0.02 | 0.02 | 0.02 | 0.02 | 0.02 |
| Ethoxy glycol | 1.00 | 1.00 | 1.00 | 1.00 | 1.00 | 1.00 | 1.00 | 1.00 | 1.00 |
| Polyacrylate | 20.00 | 20.00 | 20.00 | 20.00 | 20.00 | 20.00 | 20.00 | 20.00 | 20.00 |
| Ethanol | 30.00 | 30.00 | 30.00 | 30.00 | 30.00 | 30.00 | 30.00 | 30.00 | 30.00 |
| Hydrogenated castor oil | 0.80 | 0.80 | 0.80 | 0.80 | 0.80 | 0.80 | 0.80 | 0.80 | 0.80 |
| Phenyl trimethicone | 0.20 | 0.20 | 0.20 | 0.20 | 0.20 | 0.20 | 0.20 | 0.20 | 0.20 |
| Triethanol amine | 0.40 | 0.40 | 0.40 | 0.40 | 0.40 | 0.40 | 0.40 | 0.40 | 0.40 |
| Perfume | q.s. | q.s. | q.s. | q.s. | q.s. | q.s. | q.s. | q.s. | q.s. |
| Distilled water | to 100 | to 100 | to 100 | to 100 | to 100 | to 100 | to 100 | to 100 | to 100 |

<Formulation: Ointment>

TABLE 7

| Materials | Formulations | | | | | | C. Formulations | | |
|---|---|---|---|---|---|---|---|---|---|
| | 25 | 26 | 27 | 28 | 29 | 30 | 13 | 14 | 15 |
| Nanoemulsion of Ex. 1 | 10.0 | — | — | — | — | — | — | — | — |
| Nanoemulsion of Ex. 2 | — | 10.0 | — | — | — | — | — | — | — |
| Nanoemulsion of Ex. 3 | — | — | 10.0 | — | — | — | — | — | — |
| Nanoemulsion of Ex. 4 | — | — | — | 10.0 | — | — | — | — | — |
| Nanoemulsion of Ex. 5 | — | — | — | — | 10.0 | — | — | — | — |
| Nanoemulsion of Ex. 6 | — | — | — | — | — | 10.0 | — | — | — |
| Nanoemulsion of C. Ex. 1 | — | — | — | — | — | — | 10.0 | — | — |
| Nanoemulsion of C. Ex. 2 | — | — | — | — | — | — | — | 10.0 | — |
| Nanoemulsion of C. Ex. 3 | — | — | — | — | — | — | — | — | 10.0 |
| Capric/caprylic triglyceride | 10.0 | 10.0 | 10.0 | 10.0 | 10.0 | 10.0 | 10.0 | 10.0 | 10.0 |
| Liquid paraffin | 10.0 | 10.0 | 10.0 | 10.0 | 10.0 | 10.0 | 10.0 | 10.0 | 10.0 |
| Sorbitan sesquioleate | 6.0 | 6.0 | 6.0 | 6.0 | 6.0 | 6.0 | 6.0 | 6.0 | 6.0 |
| Octyl dodeses-25 | 9.0 | 9.0 | 9.0 | 9.0 | 9.0 | 9.0 | 9.0 | 9.0 | 9.0 |
| Cetyl ethyl hexanoate | 10.0 | 10.0 | 10.0 | 10.0 | 10.0 | 10.0 | 10.0 | 10.0 | 10.0 |
| Squalane | 1.0 | 1.0 | 1.0 | 1.0 | 1.0 | 1.0 | 1.0 | 1.0 | 1.0 |
| Salicylic acid | 1.0 | 1.0 | 1.0 | 1.0 | 1.0 | 1.0 | 1.0 | 1.0 | 1.0 |
| Glycerin | 15.0 | 15.0 | 15.0 | 15.0 | 15.0 | 15.0 | 15.0 | 15.0 | 15.0 |
| Sorbitol | 10.0 | 10.0 | 10.0 | 10.0 | 10.0 | 10.0 | 10.0 | 10.0 | 10.0 |
| Distilled water | to 100 | to 100 | to 100 | to 100 | to 100 | to 100 | to 100 | to 100 | to 100 |

Experimental Example 1

Effect on Skin Penetration

Skin penetration was evaluated for Guinea pig's skin with Frantz cell. Before test, abdominal part, a piece of skin as large as 1 cm$^2$ square was excised. The excised skin was mounted on a Frantz cell with the diameter of 0.9 cm and fixed with clamp. 0.5 ml of test sample (in case of Examples 1~9 and C. Examples 1~6, 0.05 ml of sample and distilled water; and in case of Formulations 1~30 and C. Formulations 1~15, 0.5 ml of sample only) was placed on one side of skin (donor side). The other side (receiver side) was filled with mixture of distilled water and ethanol (4:1 weight ratio). Test was performed at 32° C., which is skin temperature. Test solvent was sampled at predetermined time intervals from the receiver side, and the amounts of penetrated compound K, ginsenoside F1 and compound Y were determined by HPLC system.

The data were indicated in penetrated amount per applied concentration (μg/cm$^2$/wt %). The results are shown in Table 8a and Table 8b.

In case of purified ginseng saponin, the amount of penetrated saponin was determined. Also, in case of Bio GF1K, the amounts of penetrated compound K, ginsenoside F1 and compound Y were determined and total penetrated amounts were calculated by sum of each peak.

<HPLC Analytic Condition>
Column: C18 (ODS)
Solvent Flow: 1 ml/min
Detection UV: 203 nm
Sample test concentration 5 mg/ml
Sample injection amount: 10 μg
Eluent: Gradient condition
A: Acetonitrile/D.I. water=15/85
B: Acetonitrile/D.I. water=80/20

<Solvent Gradient Condition>

| Time (min) | A(%) | B(%) |
|---|---|---|
| 0 | 100 | — |
| 10 | 70 | 30 |
| 25 | 50 | 50 |
| 40 | — | 100 |
| 70 | — | 100 |

TABLE 8a

Penetrated amounts during elapsed time
(of Examples 1~12 and C. Examples 1~9)

| Examples | Elapsed time (hr) 0 | 4 | 8 | 12 | Comparative Examples | Elapsed time (hr) 0 | 4 | 8 | 12 |
|---|---|---|---|---|---|---|---|---|---|
| 1 | 0 | 15.15 | 29.98 | 50.13 | 1 | 0 | 3.52 | 7.11 | 15.41 |
| 2 | 0 | 15.15 | 29.98 | 50.13 | 2 | 0 | 3.66 | 7.35 | 15.06 |
| 3 | 0 | 15.45 | 39.74 | 58.43 | 3 | 0 | 3.35 | 7.04 | 14.95 |
| 4 | 0 | 15.15 | 28.98 | 33.13 | 4 | 0 | 1.42 | 1.75 | 2.45 |
| 5 | 0 | 16.02 | 32.14 | 52.21 | 5 | 0 | 1.32 | 1.68 | 2.38 |
| 6 | 0 | 14.59 | 31.25 | 49.32 | 6 | 0 | 1.51 | 1.75 | 2.55 |
| 7 | 0 | 16.02 | 32.14 | 52.21 | 7 | 0 | 0.15 | 0.45 | 0.95 |
| 8 | 0 | 13.02 | 38.64 | 55.27 | 8 | 0 | 0.20 | 0.50 | 1.02 |
| 9 | 0 | 16.02 | 26.14 | 34.21 | 9 | 0 | 0.18 | 0.43 | 0.93 |
| 10 | 0 | 14.59 | 31.25 | 49.32 | | | | | |
| 11 | 0 | 12.59 | 33.55 | 45.32 | | | | | |
| 12 | 0 | 14.59 | 20.25 | 25.32 | | | | | |

TABLE 8b

Penetrated amounts during elapsed time
(of Formulations 1~30 and C. Formulations 1~15)

| Formulations | Elapsed time (hr) 0 | 4 | 8 | 12 | Comparative Formulation | Elapsed time (hr) 0 | 4 | 8 | 12 |
|---|---|---|---|---|---|---|---|---|---|
| 1 | 0 | 12.12 | 31.00 | 50.21 | 1 | 0 | 3.51 | 6.98 | 14.68 |
| 5 | 0 | 1.21 | 1.69 | 2.44 | 2 | 0 | 0.12 | 0.42 | 0.86 |
| 6 | 0 | 2.21 | 3.86 | 5.40 | 3 | 0 | 0.48 | 1.01 | 2.03 |
| 7 | 0 | 15.98 | 31.86 | 51.97 | 4 | 0 | 3.62 | 7.21 | 14.93 |
| 11 | 0 | 1.25 | 1.61 | 2.21 | 5 | 0 | 0.14 | 0.43 | 0.90 |
| 12 | 0 | 2.24 | 3.75 | 5.11 | 6 | 0 | 0.45 | 0.97 | 1.97 |
| 13 | 0 | 14.30 | 28.59 | 49.99 | 7 | 0 | 3.23 | 6.84 | 13.83 |
| 17 | 0 | 1.25 | 1.75 | 2.35 | 8 | 0 | 0.16 | 0.47 | 0.91 |
| 18 | 0 | 2.23 | 3.65 | 5.06 | 9 | 0 | 0.50 | 1.03 | 2.11 |
| 19 | 0 | 15.21 | 31.25 | 51.21 | 10 | 0 | 3.33 | 7.13 | 15.02 |
| 23 | 0 | 1.22 | 1.85 | 2.54 | 11 | 0 | 0.16 | 0.43 | 0.92 |
| 24 | 0 | 2.12 | 3.36 | 5.35 | 12 | 0 | 0.49 | 1.11 | 2.23 |
| 25 | 0 | 12.13 | 30.99 | 51.85 | 13 | 0 | 3.45 | 7.10 | 16.02 |
| 29 | 0 | 1.23 | 1.87 | 2.13 | 14 | 0 | 0.12 | 0.44 | 0.93 |
| 30 | 0 | 2.23 | 3.45 | 5.61 | 15 | 0 | 0.48 | 0.96 | 2.06 |
| 2 | 0 | 12.12 | 31.00 | 50.21 | | | | | |
| 3 | 0 | 12.12 | 34.00 | 54.21 | | | | | |
| 4 | 0 | 12.12 | 24.00 | 35.21 | | | | | |
| 8 | 0 | 15.98 | 31.86 | 51.97 | | | | | |
| 9 | 0 | 15.98 | 37.86 | 57.93 | | | | | |
| 10 | 0 | 15.98 | 31.86 | 31.97 | | | | | |
| 14 | 0 | 14.30 | 28.59 | 49.99 | | | | | |
| 15 | 0 | 14.30 | 38.59 | 59.97 | | | | | |
| 16 | 0 | 14.30 | 28.59 | 33.99 | | | | | |
| 20 | 0 | 15.21 | 31.25 | 51.21 | | | | | |
| 21 | 0 | 14.21 | 32.25 | 53.23 | | | | | |
| 22 | 0 | 15.21 | 31.25 | 31.21 | | | | | |
| 26 | 0 | 12.13 | 30.99 | 51.85 | | | | | |
| 27 | 0 | 12.13 | 35.99 | 57.83 | | | | | |
| 28 | 0 | 12.13 | 30.99 | 31.85 | | | | | |

The result of said experiment confirmed that Examples 1~12, i.e. nanoemulsions prepared by applying nano-emulsification to metabolites of ginseng saponin, exhibited dramatic enhancement in skin penetration compared with the C. Examples. For reference, within the C. Examples, C. Examples 1~3, i.e. nanoemulsions prepared by nano-emulsification exhibited more effective skin penetration than C. Examples 4~9, i.e. simple solutions prepared by dissolving each ingredient in solvent.

By the comparison of Examples and corresponding C. Examples, it was confirmed that metabolites of ginseng saponin, i.e. compound K, ginsenoside F1 and compound Y, exhibited superior effects on skin penetration to purified ginseng saponin. This may result from specific chemical structures of compound K, ginsenoside F1 and compound Y.

In summary, metabolites of ginseng saponin, i.e. compound K, ginsenoside F1 and compound Y exhibit more effective skin penetration than purified ginseng saponin, and particularly can enhance skin penetration by emulsifying with dermotropic lecithin by nano-emulsification.

Further, these results can be confirmed in Formulations 1~30 and C. Formulations 1~15, which were prepared by formulating Examples and C. Examples. That is, skin penetration of metabolites enhanced by dermotropic lecithin and nano-emulsification was confirmed as it was within the formulations.

As shown in Table 8b, in consideration that general duration of make-up is about 4~8 hours, Examples and Formulations containing compound K, ginsenoside F1 and compound Y exhibit enhanced skin penetration 9~10 times greater than C. Examples and C. Formulations containing purified ginseng saponin.

Experimental Example 2

Effect on Proliferation of Fibroblast

Human fibroblasts were cultured on Dulbecco's Modified Eagle's Medium (DMEM) supplemented with 3.5% fetal bovine serum. The fibroblasts were seeded into 96-well microtiter plate to a density of 5,000 cells/well. In case of nanoemulsions of Examples 1~4 and of C. Example 1, test samples were prepared to adjust the concentrations of each metabolite, of Bio GF1K and of purified ginseng saponin to 1%. In case of cream of Formulations 14 and of C. Formulation 1, for each 10% of solution was prepared as test sample. The test samples were added in consecutive dilutions of 1/10 times with medium. Then, it was incubated at 37° C. for 4 days. After incubation, 0.2% of MTT (3-[4,5-dimethylthiazol-2-yl]-2,5-diphenyltetrazolium bromide) solution was added to each well, 50 µl per well, and then incubated again at 37° C. for 4 hours. The produced formazane was dissolved in dimethyl sulfoxide (DMSO) and the absorbance at 570 nm was measured with microplate reader. The proliferation of fibroblast was evaluated by comparing the absorbance with that of control group with no sample treated. The results are shown in Table 9.

TABLE 9

| Concentration of test sample | Proliferation of fibroblast (%) | | | | | | | | | |
|---|---|---|---|---|---|---|---|---|---|---|
| | Examples | | | | | Formulations | | | | |
| | 1 | 2 | 3 | 4 | C. Ex. 1 | 1 | 2 | 3 | 4 | C. Form. 1 |
| $1 \times 10^{-8}$ | 5 | 5 | 5 | 5 | 3 | 5 | 6 | 5 | 5 | 3 |
| $1 \times 10^{-7}$ | 13 | 12 | 10 | 16 | 5 | 13 | 9 | 8 | 12 | 5 |
| $1 \times 10^{-6}$ | 25 | 23 | 25 | 28 | 8 | 24 | 21 | 22 | 23 | 8 |
| $1 \times 10^{-5}$ | 47 | 45 | 43 | 45 | 13 | 45 | 41 | 39 | 44 | 12 |
| $1 \times 10^{-4}$ | 54 | 71 | 75 | 54 | 19 | 51 | 69 | 65 | 52 | 18 |
| $1 \times 10^{-3}$ | 67 | 93 | 95 | 66 | 27 | 65 | 88 | 85 | 64 | 26 |
| $1 \times 10^{-2}$ | 81 | 120 | 121 | 81 | 41 | 79 | 112 | 102 | 78 | 40 |
| $1 \times 10^{-1}$ | 98 | 151 | 153 | 98 | 48 | 96 | 135 | 123 | 95 | 45 |

As shown in Table 9, nanoemulsions of Examples 1~4 comprising the metabolites of ginseng saponin were more effective in proliferating fibroblast, in comparison with microemulsion of C. Example 1 comprising purified ginseng saponin.

Further, this result was confirmed in Formulations 1~4 and C. Formulation 1, which were prepared by formulating Examples 1~4 and C. Example 1. That is, Formulations 1~4 were more effective in proliferating fibroblast than C. Formulation 1.

Experimental Example 3

Effect on Proliferation of Keratinocyte

Proliferation of keratinocyte was evaluated by following same procedure described in Experimental Example 2. Test samples were prepared by employing Example 5, C. Example 2, Formulation 5 and C. Formulation 2, as described in Experimental Example 2. The results are shown in Table 10.

TABLE 10

| Concentration of Test sample (%) | Proliferation of keratinocyte (%) | | | |
|---|---|---|---|---|
| | Example 5 | C. Example 2 | Formulation 5 | C. Formulation 2 |
| $1 \times 10^{-8}$ | 5 | 4 | 5 | 4 |
| $1 \times 10^{-7}$ | 13 | 6 | 13 | 6 |
| $1 \times 10^{-6}$ | 18 | 7 | 18 | 7 |
| $1 \times 10^{-5}$ | 25 | 11 | 25 | 11 |
| $1 \times 10^{-4}$ | 34 | 14 | 34 | 14 |
| $1 \times 10^{-3}$ | 39 | 19 | 38 | 18 |
| $1 \times 10^{-2}$ | 45 | 23 | 44 | 21 |
| $1 \times 10^{-1}$ | 53 | 27 | 51 | 25 |

As shown in Table 10, the treatment with nanoemulsion of Example 5 comprising Bio GF1K led to about 2 times enhancement in proliferation of keratinocyte, in comparison with microemulsion of C. Example 2 comprising purified ginseng saponin.

Further, this result was confirmed in Formulation 5 and C. Formulation 2, which were prepared by formulating Example 5 and C. Example 2.

Experimental Example 4

Effect on Biosynthesis of Collagen In Vitro

Human fibroblasts were cultured on 24-well microtiter plate. As described in Experimental Example 2, in case of nanoemulsion of Example 6 and C. Example 3, test sample was added in consecutive dilutions of 1/100 times with medium. In case of cream of Formulation 6 and C. Formulation 3, test sample was added in consecutive dilutions of 1/10 times with medium. On the 3rd day, DMEM supplemented with 10% fetal bovine serum was added to each well, 0.5 ml per well, and then 10 μCi of L[2,3,4,5-3H]-proline was added. 24 hours later, the medium and the cells contained in each well were raked up and washed with 5% of trichloroacetic acid (TCA). Then, it was divided into two test tubes. 1 Unit/μl of type I collagenase was added to one tube and then incubated at 37° C. for 90 minutes. The other tube was incubated at 4° C. Then, 0.05 ml of 50% TCA was added to each tube and maintained at 4° C. for 20 minutes. The resulting solution was centrifuged at 12,000 rpm for 10 minutes. The decay per minute (dpm) of the supernatant and of the precipitate were measured with liquid scintillation counter (LSC). As to control group and test group, RCB (Relative Collagen Biosynthesis) value was calculated by the following equation 1. The results are shown in Table 11.

RCB=[collagen dpm/{(total collagen−collagen dpm)× 5.4+collagen dpm}]×100     [Equation 1]

TABLE 11

| Concentration of test sample (%) | Biosynthesis of collagen (%) | | | |
|---|---|---|---|---|
| | Example 6 | C. Example 3 | Formulation 6 | C. Formulation 3 |
| $1 \times 10^{-8}$ | 5 | 2 | 2 | 3 |
| $1 \times 10^{-7}$ | 13 | 2 | 2 | 3 |
| $1 \times 10^{-6}$ | 25 | 4 | 4 | 6 |
| $1 \times 10^{-5}$ | 33 | 6 | 6 | 9 |
| $1 \times 10^{-4}$ | 51 | 10 | 10 | 13 |
| $1 \times 10^{-3}$ | 59 | 12 | 12 | 16 |
| $1 \times 10^{-2}$ | 68 | 16 | 15 | 20 |
| $1 \times 10^{-1}$ | 74 | 20 | 18 | 25 |

As shown in Table 11, the treatment with nanoemulsion of Example 6 comprising Bio GF1K led to about 3 times enhancement in biosynthesis of collagen, in comparison with microemulsion of C. Example 3 comprising purified ginseng saponin.

Further, this result was confirmed in Formulation 6 and C. Formulation 3, which were prepared by formulating Example 6 and C. Example 3.

Experimental Example 5

Effect on Biosynthesis of Collagen In Vivo

Onto each back of hairless mice aging 42 weeks (female), Formulation 7 and C. Formulation 4 were applied in a vehicle of EtOH:PG=7:3 and patched for 3 days. After 24 hours of pause, patch was repeated for 3 days. Then, epidermal tissues were subjected to biopsy and then stained by immunohistochemical staining and haematoxylin-eosin staining for type I pN procollagen and MMP-1 (Matrix Metalloproteinase-1). Through the tissue-staining, expressions of procollagen and of MMP-1 and thickness of epidermis were observed and the results thereof were shown in FIG. 1 and FIG. 2.

Figure 2:
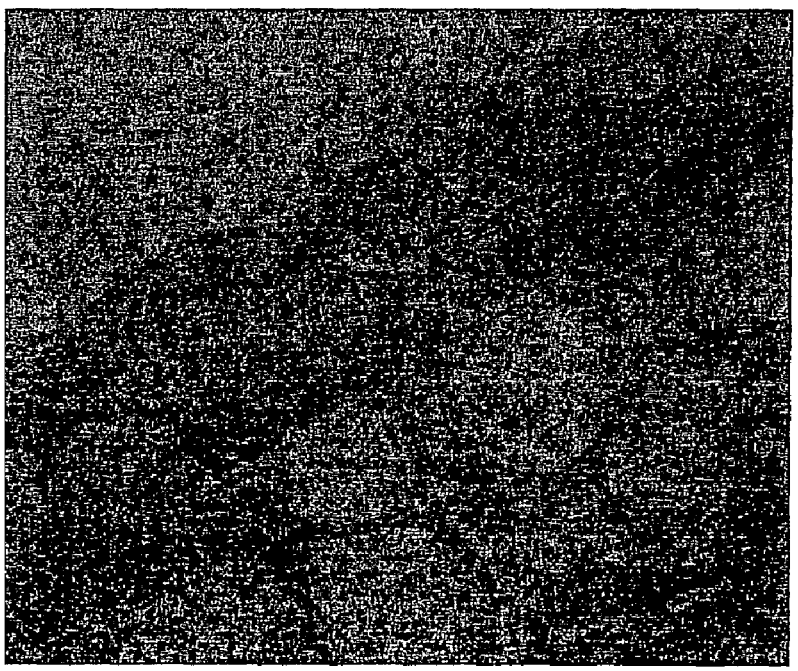
FIG. 2 is a structural photograph of epidermal cells showing the effect of Comparative Formulation 4 on biosynthesis of collagen.

In comparison of Formulation 7 with C. Formulation 4, as shown in FIG. 1 and FIG. 2, it can be confirmed that formulation of the present nanoemulsion is more effective in skin penetration of compound K, ginsenoside F1 and compound Y, so to promote biosynthesis of collagen. In case of C. Formulation 4, purified ginseng saponin is less effective in skin penetration, so to be insufficient in biosynthesis of collagen. This is because purified ginseng saponin has a structural difficulty in skin penetration, which cannot be overcome by dermotropic lecithin or by nano-emulsification.

In summary, said results confirm that metabolites of ginseng saponin, i.e. compound K, ginsenoside F1 and compound Y have a structural easiness in skin penetration, which can be maximized by dermotropic lecithin and nano-emulsification. That is, the present nanoemulsion can promote biosynthesis of collagen.

Experimental Example 6

Effect on Biosynthesis of Collagen In Vivo

Figure 3:
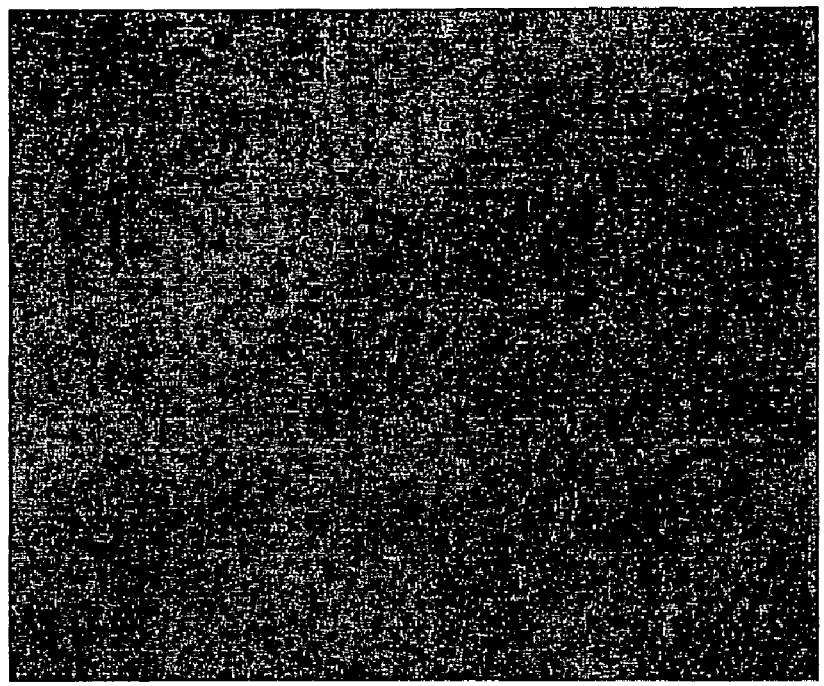
FIG. 3 is a structural photograph of epidermal cells showing the effect of Example 2 on biosynthesis of collagen.
Figure 4:
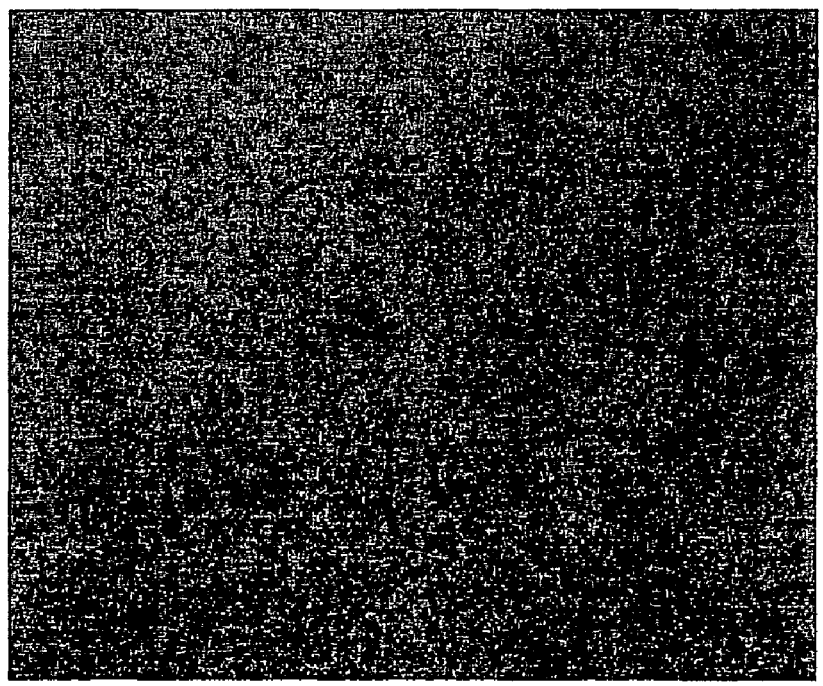
FIG. 4 is a structural photograph of epidermal cells showing the effect of Example 3 on biosynthesis of collagen.
Figure 5:
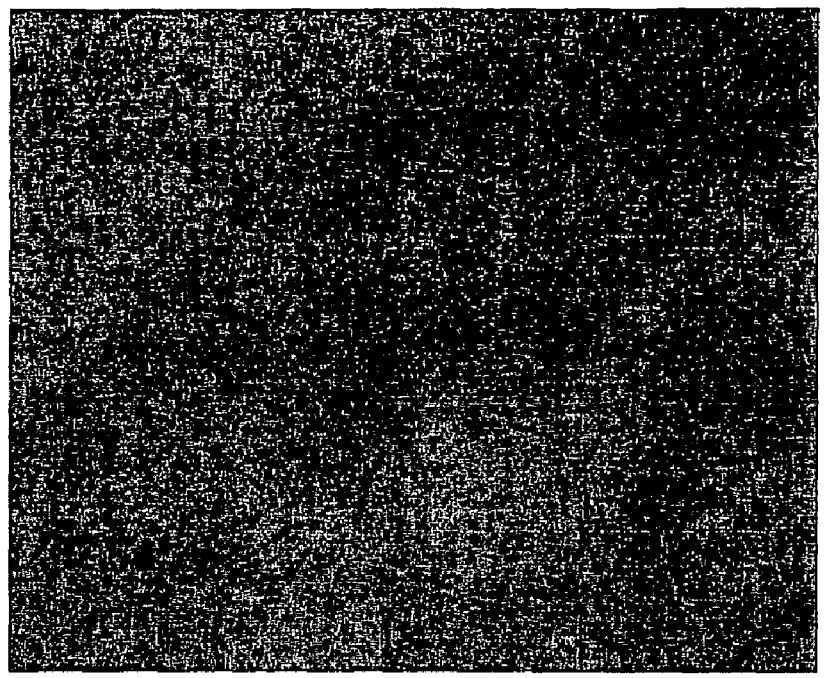
FIG. 5 is a structural photograph of epidermal cells showing the effect of Example 4 on biosynthesis of collagen.
Figure 6:
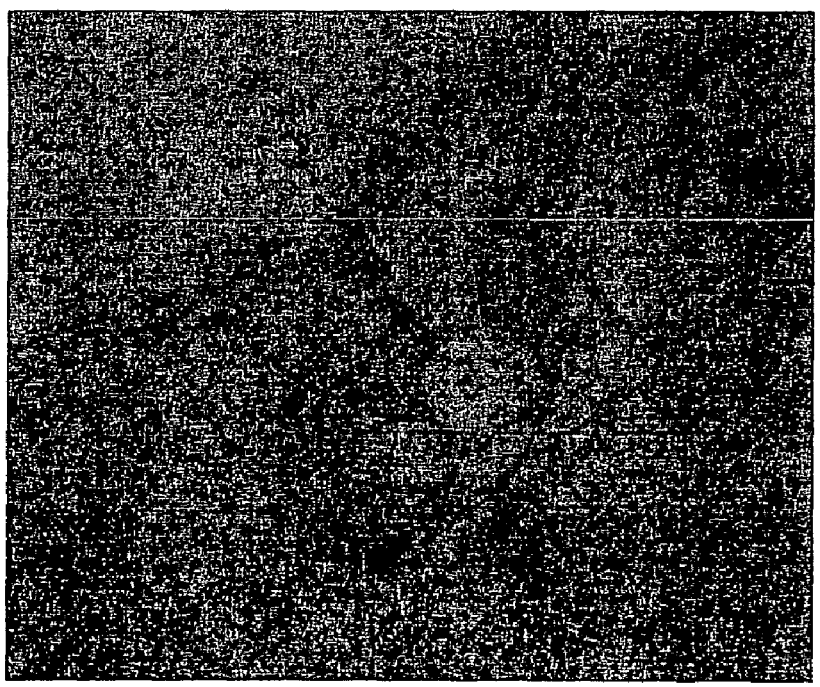
FIG. 6 is a structural photograph of epidermal cells showing the effect of Comparative Example 1 on biosynthesis of collagen.

The procedure described in Experimental Example 5 was followed by employing the nanoemulsions of Examples 2~4 and of C. Example 1 as test samples, instead of formulation, to evaluate the effect on biosynthesis of collagen. The results were shown in FIG. 3, which shows the effect of Example 2 comprising compound K; in FIG. 4, which shows the effect of Example 3 comprising ginsenoside F1; in FIG. 5, which shows the effect of Example 4 comprising compound Y; and in FIG. 6, which shows the effect of C. Example 1 comprising purified ginseng saponin.

As explained in said Experimental Example 5, from the results of Experimental Example 1 and of Experimental Example 6, it can be confirmed that the present nanoemulsion comprising the metabolites of ginseng saponin, i.e. compound K, ginsenoside F1 or compound Y, is more effective in skin penetration, so to promote biosynthesis of collagen. On the contrary, the nanoemulsion comprising purified ginseng saponin is less effective in skin penetration, so to be insufficient in biosynthesis of collagen. This is because purified ginseng saponin has a structural difficulty in skin penetration, which cannot be overcome by dermotropic lecithin or by nano-emulsification.

Experimental Example 7

Effect on Improvement of Skin Wrinkle

In order to evaluate the improvement of skin wrinkle for the composition containing the present nanoemulsion, four groups of volunteers aging 35~45 years and having facial wrinkle, thirty (30) per group, used creams of Formulation 1 and of C. Formulation 1 (Group 1); creams of Formulation 2 and of C. Formulation 1 (Group 2); creams of Formulation 3 and of C. Formulation 1 (Group 3); and creams of Formulation 4 and of C. Formulation 1 (Group 4), for 3 months. To the left face was applied the cream of Formulation and to right face was applied the cream of C. Formulation 1. The improvement of skin wrinkle was evaluated by comparing the wrinkles of eye-tail before and after using the cream. The wrinkles of eye-tail were taken with replica and measured with visiometer system (C+K) in constant temperature and humidity room set to a temperature of 24° C. and relative humidity of 40%. The improvement of skin wrinkle was calculated by the following equation 2. The results are shown in Table 12.

$$\text{Improvement of skin wrinkle } (\Delta\%) = \{(Td_i - Td_0)/Td_0\} \times 100 \quad \text{[Equation 2]}$$

(wherein, $Td_i$ is skin-wrinkle value measured after using the cream for 3 months, $Td_0$ is skin-wrinkle value measured before using the cream).

TABLE 12

| | | Wrinkle reduction ($\Delta\%$) |
|---|---|---|
| Group 1 | Formulation 1 (containing nanoemulsion of Bio GF1K) | 63 ± 15% |
| | Comparative Formulation 1 (containing nanoemulsion of ginseng saponin) | 25 ± 10% |
| Group 2 | Formulation 2 (containing nanoemulsion of compound K) | 66 ± 15% |
| | Comparative Formulation 1 | 22 ± 10% |
| Group 3 | Formulation 3 (containing nanoemulsion of ginsenoside F1) | 72 ± 15% |
| | Comparative Formulation 1 | 23 ± 10% |
| Group 4 | Formulation 4 (containing nanoemulsion of compound Y) | 56 ± 15% |
| | Comparative Formulation 1 | 21 ± 10% |

As above described, the nanoemulsion of the present invention comprises compound K, ginsenoside F1 or compound Y which have a structural effectiveness in skin penetration by removing a part of sugar moiety from ginseng saponin. Further, the present nanoemulsion has skin penetration enhanced by dermotropic emulsifier and nano-emulsification, and thereby can promote proliferation of fibroblast and biosynthesis of collagen, so to be used extensively in preventing skin-wrinkle and skin-aging.

Although preferred embodiments of the present invention have been described in detail above, it should be clearly understood that many variations of the basic inventive concepts herein taught which may appear to those skilled in the art will still fall within the spirit and scope of the present invention as defined in the appended claims.

What is claimed is:

1. A method of promoting fibroblast proliferation and collagen biosynthesis of the skin in a subject in need thereof, comprising topically applying to the subject's skin a skin-care composition containing a nanoemulsion that comprises metabolites of ginseng saponin as an effective component in an amount of 0.001%-50% by weight based on the total weight of the nanoemulsion composition, wherein said metabolites of ginseng saponin are extracted and purified from red ginseng, and wherein said metabolites of ginseng saponin are an admixture of 30-50 wt % 20-O-β-D-glucopyranosyl-20(S)-protopanaxadiol represented by the following formula 1

[Formula 1]

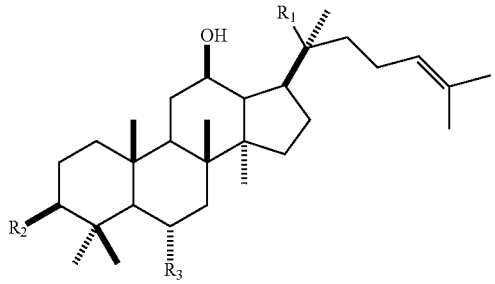

wherein, $R_1$ is O-Glc, R is OH and $R_3$ is H;

5-25 wt % 20-O-β-D-glucopyranosyl-20(S)-protopanaxatriol represented by the following formula 2

[Formula 2]

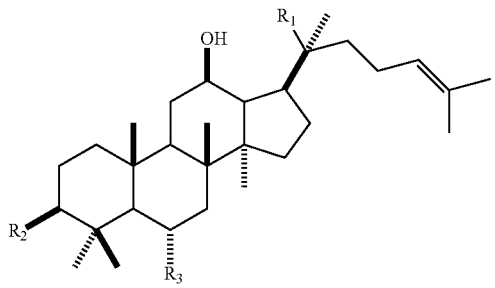

wherein, $R_1$ is O-Glc, $R_2$ is OH and $R_3$ is OH; and 5-25 wt % 20-O-[α-L-arabinopyranosyl(1→6)-β-D-glucopyranosyl]-20(S)-protopanaxadiol represented by the following formula 3

[Formula 3]

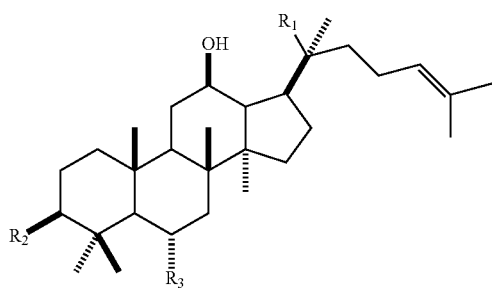

wherein $R_1$ is O-Glc$^6$-$^1$Arap, $R_2$ is OH and $R_3$ is H.

2. The method according to claim 1, wherein said nanoemulsion has a diameter of 30-500 nm.

3. The method according to claim 1, which has a formulation selected from the group consisting of skin softeners, astringents, nutrient toilet water, nutrient creams, massage creams, essences, eye creams, eye essences, cleansing creams, cleansing foams, cleansing water, powders, body lotions, body creams, body oils, body essences, make-up bases, foundation, hairdyes, shampoos, rinses, body cleansers, lotions, ointments, gels, creams, patches and sprays.

* * * * *